United States Patent [19]

Sirrenberg et al.

[11] Patent Number: 4,613,612
[45] Date of Patent: Sep. 23, 1986

[54] BENZOYLUREAS

[75] Inventors: Wilhelm Sirrenberg, Sprockhövel; Albrecht Marhold, Leverkusen; Benedikt Becker, Mettmann, all of Fed. Rep. of Germany

[73] Assignee: Bayer Aktiengesellschaft, Leverkusen, Fed. Rep. of Germany

[21] Appl. No.: 763,745

[22] Filed: Aug. 8, 1985

[30] Foreign Application Priority Data

Aug. 24, 1984 [DE] Fed. Rep. of Germany ....... 3431221

[51] Int. Cl.[4] ..................... A01N 43/32; C07D 319/20
[52] U.S. Cl. .................................... 514/456; 549/362; 549/366
[58] Field of Search ................. 549/362, 366; 514/456

[56] References Cited

U.S. PATENT DOCUMENTS 4,426,385 1/1984 Cain ................................. 549/362 X
4,536,587 8/1985 Sirrenberg et al. ................. 549/366

Primary Examiner—Dolph H. Torrence
Attorney, Agent, or Firm—Sprung Horn Kramer & Woods

[57] ABSTRACT

Insecticidally and acaricidally active novel compounds of the formula

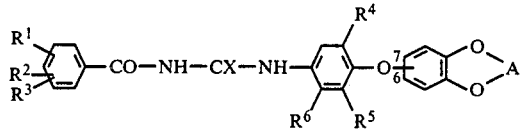

in which
A is $-CF_2-CF_2-$, $-CF_2-CHF-$ or $-CF_2-CFCl-$,
X is oxygen or sulphur,
$R^1$, $R^2$ and $R^3$ each independently is hydrogen, halogen or alkyl,
$R^4$ and $R^5$ each independently is hydrogen, halogen, alkyl or halogenoalkyl, and
$R^6$ is hydrogen, halogen or alkyl.

The benzodioxene intermediates therefor are also new.

16 Claims, No Drawings

BENZOYLUREAS

The present invention relates to new substituted 1-phenyl-3-benzoyl-(thio)ureas, several processes for their preparation and their use as agents for combating pests, in particular as insecticides and acaricides.

It is already known that certain benzoylureas have insecticidal properties (compare, for example, U.S. Pat. No. 4,139,636 or U.S. Pat. No. 3,748,356).

The new substituted 1-phenyl-3-benzoyl-(thio)-ureas of the general formula (I)

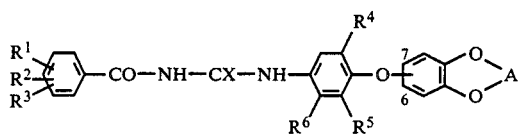

in which

A represents the —$CF_2$—$CF_2$—, —$CF_2$—CHF— or —$CF_2$—CFCl— group,

X represents oxygen or sulphur, $R^1$, $R^2$ and $R^3$ are identical or different and represent hydrogen, halogen or alkyl, $R^4$ and $R^5$ are identical or different and represent hydrogen, halogen, alkyl or halogenoalkyl and $R^6$ represents hydrogen, halogen or alkyl, have been found.

The new compounds have powerful biological, in particular insecticidal, properties which enable them to be used as agents for combating pests, in particular as insecticides and acaricides.

It has furthermore been found that the new substituted 1-phenyl-3-benzoyl-(thio)ureas of the general formula (I) are obtained by a process in which (a) substituted anilines of the general formula (II)

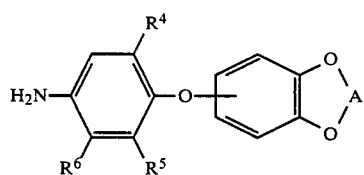

in which

A, $R^4$, $R^5$ and $R^6$ have the abovementioned meanings, are reacted with benzoyl iso(thio)cyanates of the general formula (III)

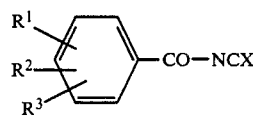

in which

X, $R^1$, $R^2$ and $R^3$ have the abovementioned meanings, if appropriate in the presence of a diluent, or (b) substituted phenyl iso(thio)cyanates of the general formula (IV)

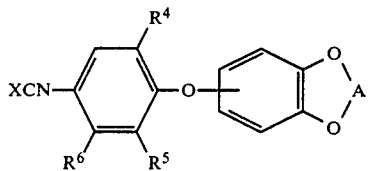

in which

A, X, $R^4$, $R^5$ and $R^6$ have the abovementioned meanings, are reacted with benzoic acid amides of the general formula (V)

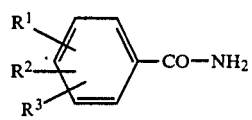

in which $R^1$, $R^2$ and $R^3$ have the abovementioned meanings, if appropriate in the presence of a catalyst and if appropriate in the presence of a diluent.

The alkyl radicals $R^1$, $R^2$, $R^3$, $R^4$, $R^5$ and $R^6$ can be identical or different and denote straight-chain or branched alkyl with 1 to 12, preferably 1 to 6, in particular 1 to 4 and very particularly preferably 1 or 2, carbon atoms. Examples which may be mentioned are methyl, ethyl, n-propyl, i-propyl, n-butyl, i-butyl, sec.-butyl and tert.-butyl.

The methyl group is particularly preferred.

The halogenoalkyl radicals $R^4$ and $R^5$ can be identical or different and in each case contain, in the alkyl part, straight-chain or branched alkyl with 1 to 6, preferably 1 to 4 and in particular 1 or 2, carbon atoms and preferably 1 to 6, in particular 1 to 4, halogen atoms, the halogen atoms being identical or different and preferred halogen atoms being fluorine, chlorine or bromine, in particular fluorine. Examples which may be mentioned are trifluoromethyl, chlorodifluoromethyl, trifluoroethyl, chlorotrifluoroethyl and tetrafluoroethyl. The trifluoromethyl group is particularly preferred.

A preferably represents the —$CF_2$—$CF_2$— group.

Halogen in the definition of $R^1$, $R^2$, $R^3$, $R^4$, $R^5$ and $R^6$ denotes fluorine, chlorine, bromine or iodine, preferably fluorine, chlorine or bromine, in particular fluorine or chlorine.

Preferably, at least one of the radicals $R^1$, $R^2$ and $R^3$ in the new compounds is other than hydrogen.

X preferably represents oxygen.

$R^2$ and $R^6$ preferably denote hydrogen.

$R^1$ is preferably in the 2-position, $R^2$ is preferably in the 4-position and $R^3$ is preferably in the 6-position in the phenyl ring of the benzoyl part.

The benzodioxene radical is preferably bonded in the 6- or 7-position to the phenoxy group on the oxygen atom, mixtures of the 6- and 7-isomers also being possible.

The new compounds of the general formula (I) have properties which enable them to be used as agents for combating pests, and in particular they are distinguished both by an outstanding insecticidal activity and by a good acaricidal activity. In this respect, they differ from the known benzoylureas, for which an insecticidal activity is known.

The invention preferably relates to new compounds of the general formula (I) in which A represents the —$CF_2$—$CF_2$—, —$CF_2$—CHF— or —$CF_2$—CFCl— group, X represents oxygen or sulphur, $R^1$ represents hydrogen, halogen or $C_1$-$C_6$-alkyl, $R^2$ and $R^3$ are identical or different and represent hydrogen, halogen or $C_1$-$C_6$-alkyl, $R^4$ and $R^5$ are identical or different and represent hydrogen, halogen, $C_1$-$C_6$-alkyl or $C_1$-$C_6$-halogenoalkyl and $R^6$ represents hydrogen, halogen or $C_1$-$C_6$-alkyl.

Particularly preferred compounds of the general formula (I) are those in which

A represents the —$CF_2$—$CF_2$—, —$CF_2$—CHF— or —$CF_2$—CFCl— group,

X represents oxygen or sulphur, $R^1$ represents halogen or $C_1$-$C_4$-alkyl, $R^2$ and $R^3$ are identical or different and represent hydrogen, halogen or $C_1$-$C_4$-alkyl, $R^4$ and $R^5$ are identical or different and represent hydrogen, halogen, $C_1$-$C_4$-alkyl or $C_1$-$C_4$-halogenoalkyl and $R^6$ represents hydrogen.

Very particularly preferred compounds of the general formula (I) are those in which A represents the —$CF_2$—$CF_2$—, —$CF_2$CHF— or —$CF_2$—CFCl— group, X represents oxygen or sulphur, preferably oxygen, $R^1$ represents fluorine, chlorine, bromine or methyl, $R^2$ and $R^3$ are identical or different and represent hydrogen, fluorine or chlorine, $R^4$ and $R^5$ are identical or different and represent hydrogen, fluorine, chlorine, methyl or trifluoromethyl and $R^6$ represents hydrogen.

A particularly good activity is shown by compounds of the general formula (I) in which A represents the —$CF_2$—$CF_2$— group, X represents oxygen or sulphur, $R^1$ is in the 2-position and represents chlorine or fluorine, $R^2$ represents hydrogen, $R^3$ is in the 6-position and represents hydrogen, fluorine or chlorine, $R^4$ and $R^5$ are identical or different and represent hydrogen, chlorine, methyl or trifluoromethyl and $R^6$ represents hydrogen.

If 4-(2,2,3,3-tetrafluoro-benzo-1,4-dioxen-6-oxy)-aminobenzene and 2,6-difluorobenzoyl isocyanate are used as starting substances in process variant (a), the course of the reaction can be represented by the following equation:

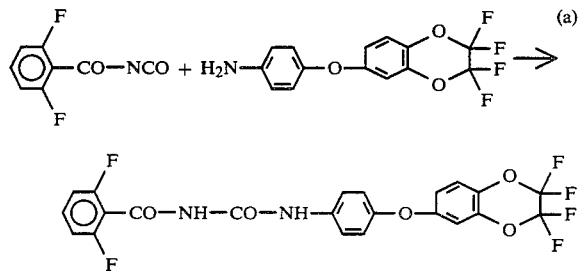

If 4-(2,2,3,3-tetrafluoro-benzo-1,4-dioxen-6-oxy)-phenyl isocyanate and 2,6-difluoro-benzamide are used as starting substances in process variant (b), the course of the reaction can be represented by the following equation:

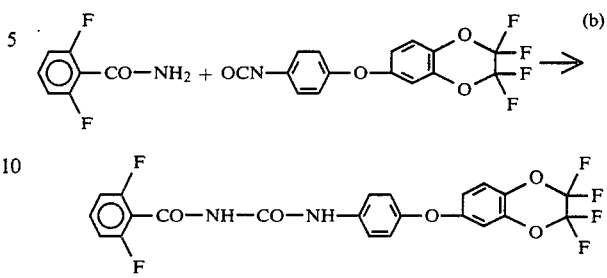

The starting compounds of the general formulae (II) and (IV) are new. Their preparation processes are described below.

The starting compounds of the general formula (III) are known or are obtainable by generally known methods.

Examples which may be mentioned of the compounds of the formula (III) are: 2-fluoro-, 2-chloro-, 2-bromo-, 2-methyl-, 2,6-difluoro-, 2,6-dichloro-, 2-chloro-6-fluoro-, 2-chloro-4-fluoro-, 2,4-difluoro-, 2,4-dichloro-, 2,4,6-trichloro-, 4-fluoro-, 4-chloro, 4-bromo- and 4-methyl-benzoyl isocyanate and -benzoyl isothiocyanate.

The starting compounds of the general formula (V) are likewise known or they are obtainable by generally known methods.

Examples which may be mentioned of the compounds of the formula (V) are: 2-fluoro-, 2-chloro-, 2-bromo-, 2-methyl-, 2,6-difluoro-, 2,6-dichloro- and 2-chloro-6-fluoro-benzoic acid amide.

Possible diluents in carrying out process variants (a) and (b) are virtually all the inert organic solvents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylacetamide and N-methyl-pyrrolidone, and tetramethylene sulphone.

Catalysts which can be used for the reaction according to process variant (b) are preferably tertiary amines, such as triethylamine and 1,4-diazabicyclo-[2,2,2]-octane, and organic tin compounds, such as, for example, dibutyl-tin dilaurate. However, the addition of such catalysts is not necessary.

The reaction temperature can be varied within a substantial range in process variants (a) and (b). In general, process variant (a) is carried out between 20° and 180° C., preferably between 40° and 120° C., and process variant (b) is carried out between 20° and 200° C., preferably between 60° and 190° C. The process variants according to the invention are in general carried out under normal pressure.

For carrying out the process variants according to the invention, the starting substances are usually employed in approximately equimolar amounts. An excess of one or the other of the reaction components provides no substantial advantages.

The reaction products are worked up by customary methods, for example by filtering off the precipitated product with suction or by dissolving undesirable by-products out of the reaction mixture. They are characterized by their melting point.

The starting compounds of the general formulae (II) and (IV) are new. They can be summarized by the following general formula (VI):

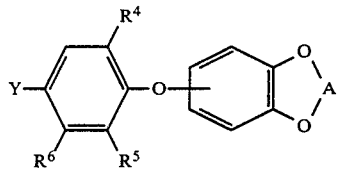

in which
Y represents the $NH_2$ or NCX group and
A, X, $R^4$, $R^5$ and $R^6$ have the abovementioned meanings (the abovementioned preference ranges also applying here).

The compounds of the general formula (VI) and processes for their preparation are part of the present invention.

The compounds of the general formula (VI) are obtained by a process in which compounds of the general formula (VII)

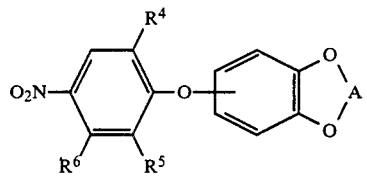

in which
A, $R^4$, $R^5$ and $R^6$ have the abovementioned meaning, are reduced catalytically or with metals or metal salts to give the compounds of the general formula (II)

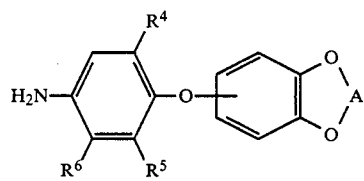

in which
A, $R^4$, $R^5$ and $R^6$ have the abovementioned meaning, and the compounds of the general formula (II) are isolated and, if appropriate, these compounds are reacted with phosgene or thiophosgene to give the compounds of the general formula (IV)

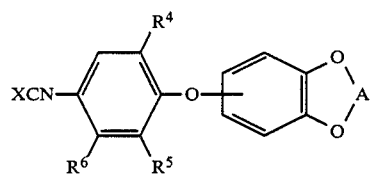

in which
A, X, $R^4$, $R^5$ and $R^6$ have the abovementioned meaning.

All the customary catalysts are possible for the catalytic hydrogenation of the nitro compounds of the general formula (VII), such as Raney nickel, platinum, platinum oxide and palladium, it also being possible for the catalysts to be present on supports, for example active charcoal or aluminum oxide.

Possible solvents are all the solvents which are usually employed for hydrogenation reactions, such as alcohols, for example methanol, hydrocarbons, such as toluene, or ethers, for example dioxane and tetrahydrofuran.

In general, increased hydrogen pressures, preferably of between 10 and 80 bar, are employed. The hydrogenation is preferably carried out at temperatures from 10° to 100° C., in particular 20° to 80° C. The compounds of the general formula (II) are worked up and isolated in the customary manner.

The reduction of the nitro compounds of the general formula (VII) can also be carried out in the customary manner with metals, such as iron and tin, and salts thereof, preferably $SnCl_2$. The reduction with $SnCl_2$ is preferably carried out in a mixture of aqueous HCl and dioxane (or also under anhydrous conditions in alcohols, such as ethanol) at temperatures between 20° and 100° C. Analogously, it is also possible to use iron in the form of iron powder or iron filings, temperatures of 80° to 100° C. preferably being employed. The compounds of the general formula (II) are in this case also worked up and isolated in the customary manner.

The compounds of the general formula (IV) can easily be obtained from the compounds of the general formula (II) and phosgene or thiophosgene by the customary phosgenation methods. The solvents used are preferably optionally halogenated aromatic or araliphatic solvents, such as chlorotoluene, toluene or xylene.

The phosgenation is preferably carried out at temperatures between 0° and 150° C., in particular between 0° and 130° C. The compounds of the general formula (IV) are worked up and isolated by generally customary methods.

The compounds of the general formula (VII) are new. These compounds and a process for their preparation are also part of the present invention.

The compounds of the general formula (VII)

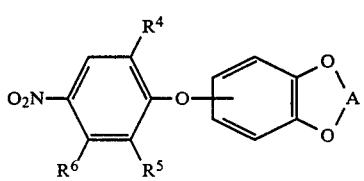

in which
A, $R^4$, $R^5$ and $R^6$ have the abovementioned meaning (the abovementioned preferred definitions also applying here)
are obtained by a process in which the compounds of the general formula (VIII)

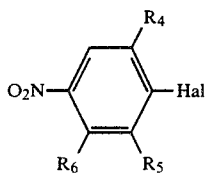

in which
Hal represents halogen (preferably fluorine, chlorine or bromine, in particular chlorine or bromine),
are reacted with compounds of the general formula (IX)

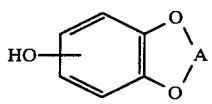

in which
A has the abovementioned meaning,
if appropriate in the form of their salts (preferably alkali metal or alkaline earth metal salts), or if appropriate in the presence of a base.

The reaction of the compounds of the general formulae (VIII) and (IX) to give the compounds of the general formula (VII) is carried out in the presence of an organic solvent, polar organic solvents being preferred, such as amides, for example dimethylacetamide and dimethylformamide, or dimethylsulphoxide.

The reaction temperatures are 100° to 180° C., preferably 110° to 130° C., with a reaction time of several hours (preferably 10 to 20 hours). The reactants can be employed in molar amounts. However, an excess of one or the other of the starting compounds does not produce adverse results.

A base, preferably an alkali metal hydroxide or alkaline earth metal hydroxide (preferably in an equivalent amount), such as sodium hydroxide, potassium hydroxide or calcium hydroxide, is advantageously added. It is also possible to employ the compounds of the general formula (IX) in the form of their salts, preferably the alkali metal or alkaline earth metal salts, particularly preferably the sodium or potassium salts. The compounds of the general formula (VII) are worked up and isolated by generally customary methods.

The compounds of the general formula (IX) are new and are part of the present invention, as is a process for their preparation.

The compounds of the general formula (IX) are obtained by a process in which the compounds of the general formula (X)

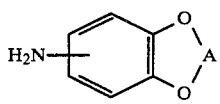

in which
A has the abovementioned meaning,
are diazotized and the diazonium salt formed is decomposed by boiling in acid solution, if appropriate in the presence of a copper salt, and the resulting compounds of the general formula (IX) are isolated in the customary manner.

The compounds of the general formula (X) are diazotized here by generally customary methods. A mixture of sulphuric acid with acetic acid and/or water is preferably used as the diluent. The diazotization is preferably carried out with sodium nitrite at temperatures from 0° to 10° C., the mixture advantageously being allowed to after-react at 20° to 50° C. for 30 to 60 minutes. To decompose the diazonium salt formed ("decomposition by boiling"), the product is heated to 120° to 180° C. in aqueous sulphuric acid, during which the sulphuric acid concentration should be 40 to 65%. To achieve high decomposition temperatures, up to about 30% by weight of alkali metal sulphate, preferably sodium sulphate, can be added to the sulphuric acid. The reaction can be facilitated by the addition of copper salts (such as CuO or $CuSO_4$) in an amount of about 5 to 20% by weight, based on the sulphuric acid. The hydroxybenzodioxene formed is distilled off continuously from the reaction mixture by steam distillation and is isolated by generally customary methods.

The starting compounds of the general formula (X) are known or they can be prepared by known methods (compare European Patent Specification No. 11,179).

The new starting substances of the general formulae (II), (IV), (VII) and (IX) can be summarized by the general formula (XI):

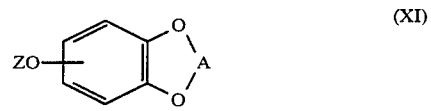

in which
A represents the $-CF_2-CF_2-$, $-CF_2-CHF-$ or $-CF_2-CFCl-$ group and
Z represents hydrogen or a

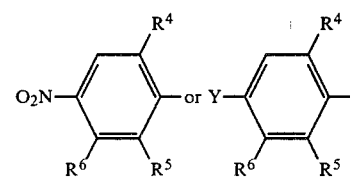

radical,
wherein
$R^4$ and $R^5$ are identical or different and represent hydrogen, halogen, alkyl or halogenoalkyl,
$R^6$ represents hydrogen, halogen or alkyl and
Y represents the $NH_2$ or NCX group,
wherein
X denotes oxygen or sulphur.

The active compounds of the general formula (I) are well tolerated by plants, have a favorable level of toxicity to warm-blooded animals, and are suitable for combating animal pests, especially insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec.

From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp. From the order of the Anoplura, for example, *Phylloxera vastatrix*, Pemphigus spp., *Pediculus humanus corporis,* Haematopinus spp. and Linognathus spp. From the order of the Mallophage, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma Lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata Lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citerlla,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferane, Clysia ambiguella, Homona magnanima* and *Tortrix viridana*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp. From the order of the Arachnida, for example, *Scorpio maurus* and *Latrodectus mactans*.

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phosoholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating undesirable pests in the field of livestock husbandry and stock breeding, it being possible to achieve better results, for example higher milk yields, higher weight, a more attractive animal coat, a longer life and the like, by combating the pests.

The active compounds according to the invention are used in these fields in a known manner, for example by external application in the form of, for example, dipping, spraying, pouring on and spotting on.

The activity of the compounds of the general formula (I) according to the invention may be illustrated with the aid of the following biological examples:

EXAMPLE A

Plutella Test

Solvent: 15 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*), as long as the leaves are still moist.

After the specified period of time, the destruction in % is determined. 100% means that all the caterpillars have been killed; 0% means that none of the caterpillars have been killed.

In this test, for example, the compounds of examples 17, 18 and 27 showed a destruction of 100% after 7 days, at an active compound concentration of 0.001%.

EXAMPLE B

Laphygam Test

Solvent: 15 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Laphygma frugiperda*), as long as the leaves are still moist.

After the specified period of time, the destruction in % is determined. 100% means that all the caterpillars have been killed; 0% means that none of the caterpillars have been killed.

In this test, for example, the compounds of Examples 6, 18 and 25 showed a destruction of 100% after 7 days, at an active compound concentration of 0.0001%.

EXAMPLE C

Tetranychus Test (Resistant)

Solvent: 15 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified period of time, the destruction in % is determined. 100% means that all the spider mites have been killed; 0% means than none of the spider mites have been killed.

In this test, for example, the compounds of Examples 1, 2, 4, 6 to 9, 11, 15, 18, 19 and 22 to 27 showed a destruction of over 95% after 10 days, at an active compound concentration of 0.1%.

The preparation of the compounds of the general formula (I) according to the invention may be illustrated with the aid of the following examples:

EXAMPLE 1

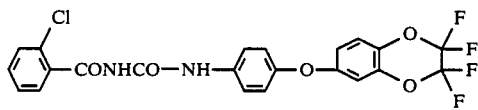

A solution of 1.82 g of 2-chlorobenzoyl isocyanate in 10 ml of dry toluene is added to a solution of 3.15 g of 4-(2,2,3,3-tetrafluoro-benzo-1,4-dioxen-6-oxy)amino-benzene in 40 ml of dry toluene at 60° C. The mixture is stirred at 80° C. for ½ hour and then concentrated in vacuo. After addition of a little petroleum ether, the precipitated product is filtered off with suction. 4.4 g of the above benzoylurea (88.5% of theory) of melting point 175° C. are obtained.

The following compounds of the general formula (I) are obtained analogously to Example 1:

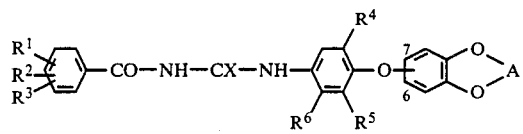

EXAMPLE 1A

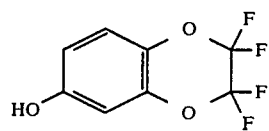

A mixture of 2,400 ml of acetic acid and 290 ml of concentrated sulphuric acid is taken, 316 g of 6-amino-2,2,3,3-tetrafluoro-1,4-benzodioxene are added and the mixture is cooled to 5° C. Diazotization is then carried out with 102 g of sodium nitrite in 360 ml of water and, after the end of the addition, the mixture is subsequently stirred at 20° C. for 30 minutes and at 50° C. for 30 minutes.

To decompose the diazonium salt by boiling, 2,900 ml of 50% strength sulphuric acid are taken with 220 g of copper sulphate.$5H_2O$ and 14 g of CuO under reflux and the diazonium salt solution is added dropwise. The corresponding phenol is immediately distilled off by steam being passed in. The phenol is extracted from the distillate with methylene chloride and the organic phase is dried and distilled.

230 g $\triangleq$ 72% of theory of 6-hydroxy-2,2,3,3-tetrafluorobenzodioxene are obtained, boiling point: 102°-3° C./20 mbar, melting point=60°-2° C.

| A = —$CF_2$—$CF_2$—; benzodioxene radical in the 6-position |||||||||
| --- | --- | --- | --- | --- | --- | --- | --- | --- |
| Example No. | $R^1$ | $R^2$ | $R^3$ | $R^4$ | $R^5$ | $R^6$ | X | melting point °C. | Yield: % of theory |
| 2 | 2-F | H | 6-F | H | H | H | O | 188 | 98.5 |
| 3 | 2-Cl | 4-F | H | H | H | H | O | 152 | 97.0 |
| 4 | 2-F | H | 6-F | H | H | H | S | 172 | 86.5 |
| 5 | 2-Cl | H | 6-Cl | H | H | H | S | 163 | 83.0 |
| 6 | 2-F | H | 6-F | Cl | H | H | O | 162 | 80.5 |
| 7 | 2-Cl | H | H | $CH_3$ | H | H | O | 187 | 92.5 |
| 8 | 2-F | H | 6-F | $CH_3$ | H | H | O | 168 | 70.0 |
| 9 | 2-Cl | H | 6-F | $CH_3$ | H | H | O | 116 | 97.5 |
| 10 | 2-Cl | 4-F | H | $CH_3$ | H | H | O | 162 | 90.5 |
| 11 | 2-F | H | 6-F | $CH_3$ | H | H | S | 147 | 66.0 |
| 12 | 2-Cl | H | H | $CF_3$ | H | H | O | 134 | 60.0 |
| 13 | 2-F | H | 6-F | $CF_3$ | H | H | O | 138 | 76.0 |
| 14 | 2-Cl | H | 6-F | $CF_3$ | H | H | O | 153 | 94.5 |
| 15 | 2-F | H | 6-F | $CF_3$ | H | H | S | 165 | 88.0 |
| 16 | 2-Br | H | H | $CF_3$ | H | H | S | 163 | 83.0 |
| 17 | 2-Cl | H | H | Cl | Cl | H | O | 199 | 90.0 |
| 18 | 2-F | H | 6-F | Cl | Cl | H | O | 196 | 90.0 |
| 19 | 2-Cl | H | 6-F | Cl | Cl | H | O | 189-190 | 84.0 |
| 20 | 2-Cl | 4-F | H | Cl | Cl | H | O | 184 | 92.5 |
| 21 | 2-$CH_3$ | H | H | Cl | Cl | H | O | 205 | 99.0 |
| 22 | 2-F | H | 6-F | Cl | Cl | H | S | 141 | 91.5 |
| 23 | 2-Cl | H | 6-F | Cl | Cl | H | S | 198 | 93.5 |
| 24 | 2-Cl | H | H | $CH_3$ | $CH_3$ | H | O | 183 | 85.0 |
| 25 | 2-F | H | 6-F | $CH_3$ | $CH_3$ | H | O | 180-182 | 95.0 |
| 26 | 2-Cl | H | 6-F | $CH_3$ | $CH_3$ | H | O | 181 | 92.5 |
| 27 | 2-F | H | 6-F | $CH_3$ | $CH_3$ | H | S | 141 | 85.0 |
| 28 | 2-Cl | H | 6-F | $CH_3$ | $CH_3$ | H | S | 125 | 100.0 |
| 29 | 2-Cl | H | 6-Cl | $CH_3$ | $CH_3$ | H | S | 163 | 81.5 |
| 30 | 2-Cl | H | H | $CF_3$ | $CF_3$ | H | O | 146 | 97.5 |
| 31 | 2-F | H | 6-F | $CF_3$ | $CF_3$ | H | O | 165 | 86.5 |
| 32 | 2-Cl | H | 6-F | $CF_3$ | $CF_3$ | H | O | 172 | 72.5 |
| 33 | 2-Cl | 4-F | H | $CF_3$ | $CF_3$ | H | O | 151 | 83.0 |
| 34 | 2-F | H | 6-F | $CF_3$ | $CF_3$ | H | S | 147 | 73.5 |

The preparation of the compounds of the general formula (IX) may be illustrated by the following examples:

EXAMPLE 2A

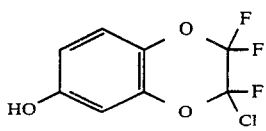

6-Hydroxy-3-chloro-2,2,3-trifluoro-1,4-benzodioxene is obtained from 6-amino-3-chloro-2,2,3-trifluoro-1,4-benzodioxene analogously to the instructions in Example 1A.

Boiling point: 112°-5° C./20 mbar.

EXAMPLE 2B

A mixture of 6- and 7-hydroxy-2,2,3,-trifluoro-1,4-benzodioxene is obtained from a 50:50 mixture of 6- and 7-amino-2,2,3-trifluoro-1,4-benzodioxene analogously to Example 1A.

Boiling point: 91° C./10 mbar

The preparation of the compounds of the general formula (VII) may be illustrated with the aid of the following examples:

EXAMPLE 1B

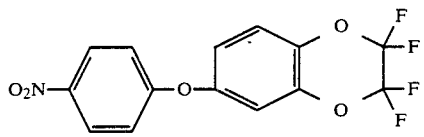

A suspension of 8.2 g of KOH powder in 15 ml of DMSO (=dimethylsulphoxide) is added to a solution of 3.15 g of 2,2,3,3-tetrafluoro-6-hydroxy-benzo-1,4-dioxene in 200 ml of DMSO and the mixture is stirred at room temperature for 1 hour. 18.9 g of 4-nitrochlorobenzene are added to the solution and the mixture is stirred at 110°-120° C. for 14 hours. After cooling, 1.5 l of water are added and the solution is extracted 3 times with 250 ml of ethylene chloride. The combined ethylene chloride extracts are washed twice with water and then dried. The dried solution is concentrated in vacuo and the oil which remains is triturated with cold petroleum ether, whereupon it crystallizes.

31.7 g of the above compound of melting point 64° C. are obtained.

The compounds of the following examples are obtained analogously:

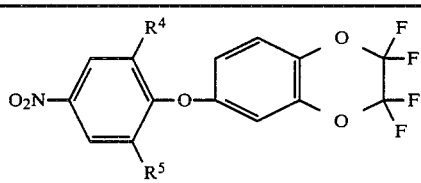

(XII)

| Example No. | R⁴ | R⁵ | melting point (°C.) or $n_D^{20}$ | Yield: % of theory |
|---|---|---|---|---|
| 2B | H | H | 64 | 76 |
| 3B | CH₃ | H | 81 | 72.5 |
| 4B | CF₃ | H | 1.5015 | 91.5 |
| 5B | Cl | Cl | 61 (1.5515) | 85.5 |
| 6B | CH₃ | CH₃ | 111 | 78 |
| 7B | CF₃ | CF₃ | 1.4750 | 89.5 |

The preparation of the compounds of the general formula (II) may be illustrated with the aid of the following examples:

EXAMPLE 1C

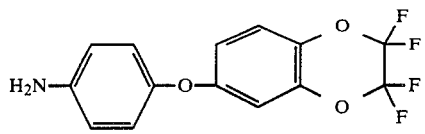

29.3 g of 4-(2,2,3,3-tetrafluoro-benzo-1,4-dioxen-6-oxy)-nitrobenzene are dissolved in 250 ml of ethanol. A solution of 92 g of SnCl₂.2H₂O in 108 ml of concentrated hydrochloric acid is added dropwise thereto at 10°-20° C. The mixture is stirred at 80° C. for 4 hours and then cooled. It is stirred into 1.5 l of ice-water in which 180 g of sodium hydroxide are dissolved. This solution is extracted several times with ethylene chloride and the combined extracts are washed with water. The ethylene chloride solution is dried and the solvent is then evaporated off in vacuo.

24.4 g of the substance are obtained as an oil of refractive index $n^{20}$ 1.5332.

The compounds of the following examples can be obtained analogously:

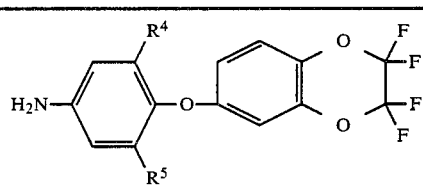

(XIII)

| Example No. | R⁴ | R⁵ | melting point (°C.) or $n_D^{20}$ | Yield: % of theory |
|---|---|---|---|---|
| 2C | H | H | 1.5332 | 86 |
| 3C | CH₃ | H | 80 | 76 |
| 4C | CF₃ | H | 1.5015 | 92 |
| 5C | Cl | Cl | 136 | 81.5 |
| 6C | CH₃ | CH₃ | 84 | 95.5 |
| 7C | CF₃ | CF₃ | 1.4770 | 83 |

It is understood that the specification and examples are illustrative but not limitative of the present invention and that other embodiments within the spirit and scope of the invention will suggest themselves to those skilled in the art.

We claim:

1. A compound of the formula

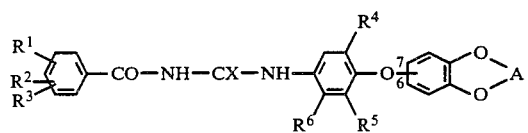

in which

A is —CF₂—CF₂—, —CF₂—CHF— or —CF₂—CFCl—,

X is oxygen or sulphur,

R¹, R² and R³ each independently is hydrogen, halogen or alkyl,

R⁴ and R⁵ each independently is hydrogen, halogen, alkyl or halogenoalkyl, and

R⁶ is hydrogen, halogen or alkyl.

2. A compound according to claim 1, in which
R$^1$ is hydrogen, halogen or C$_1$-C$_6$-alkyl,
R$^2$ and R$^3$ each independently is hydrogen, halogen or C$_1$-C$_6$-alkyl,
R$^4$ and R$^5$ each independently is hydrogen, halogen, C$_1$-C$_6$-alkyl or C$_1$-C$_6$-halogenoalkyl, and
R$^6$ is hydrogen, halogen or C$_1$-C$_6$-alkyl.

3. A compound according to claim 1, in which
R$^1$ is halogen or C$_1$-C$_4$-alkyl,
R$^2$ and R$^3$ each independently is hydrogen, halogen or C$_1$-C$_4$-alkyl,
R$^4$ and R$^5$ each independently is hydrogen, halogen, C$_1$-C$_4$-alkyl or C$_1$-C$_4$-halogenoalkyl, and
R$^6$ is hydrogen.

4. A compound according to claim 1, in which
X is oxygen,
R$^1$ is fluorine, chlorine, bromine or methyl,
R$^2$ and R$^3$ each independently is hydrogen, fluorine or chlorine,
R$^4$ and R$^5$ each independently is hydrogen, fluorine, chlorine, methyl or trifluoromethyl, and
R$^6$ is hydrogen.

5. A compound according to claim 1, wherein such compound is N-(2,6-difluorobenzoyl)-N'-[4-(2,2,3,3-tetrafluorobenzo-1,4-dioxen-6-oxy)-phenyl]-urea of the formula

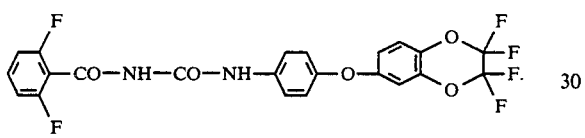

6. A compound according to claim 1, wherein such compound is N-(2,6-difluorobenzoyl)-N'-[4-(2,2,3,3-tetrafluorobenzo-1,4-dioxen-6-oxy)-phenyl]-thiourea of the formula

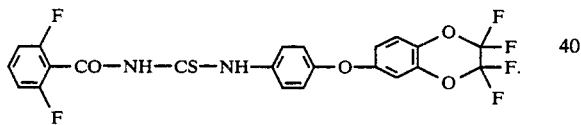

7. A compound according to claim 1, wherein such compound is N-(2,6-difluorobenzoyl)-N'-[3-methyl-4-(2,2,3,3-tetrafluorobenzo-1,4-dioxen-6-oxy)-phenyl]-urea of the formula

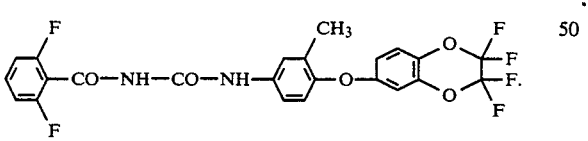

8. A compound according to claim 1, wherein such compound is N-(2-chloro-6-fluorobenzoyl)-N'-[3-methyl-4-(2,2,3,3-tetrafluorobenzo-1,4-dioxen-6-oxy)-phenyl]-urea of the formula

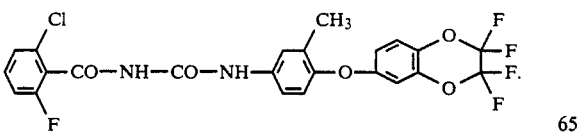

9. A compound according to claim 1, wherein such compound is N-(2,6-difluorobenzoyl)-N'-[3,5-dimethyl-4-(2,2,3,3-tetrafluorobenzo-1,4-dioxen-6-oxy)-phenyl]-urea of the formula

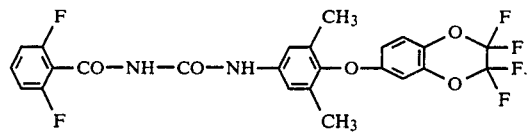

10. An insecticidal or acaricidal composition comprising an insecticidally or acaricidally effective amount of a compound according to claim 1 in admixture with a diluent.

11. A method of combating insects or acarids which comprises applying thereto or to a habitat thereof an insecticidally or acaricidally effective amount of a compound according to claim 1.

12. The method according to claim 11, wherein such compound is
N-(2,6-difluorobenzoyl)-N'-[4-(2,2,3,3-tetrafluorobenzo-1,4-dioxen-6-oxy)-phenyl]-urea,
N-(2,6-difluorobenzoyl)-N'-[4-(2,2,3,3-tetrafluorobenzo-1,4-dioxen-6oxy)-phenyl]-thiourea,
N-(2,6-difluorobenzoyl)-N'-[3-methyl-4-(2,2,3,3-tetrafluorobenzol-1,4-dioxen-6-oxy)-phenyl]-urea,
N-(2-chloro-6-fluorobenzoyl)-N'-[3-methyl-4-(2,2,3,3-tetrafluorobenzo-1,4-dioxen-6-oxy)-phenyl]-urea or
N-(2,6-difluorobenzoyl)-N'-[3,5-dimethyl-4-(2,2,3,3-tetrafluorobenzo-1,4-dioxen-6-oxy)-phenyl]-urea.

13. A compound of the formula

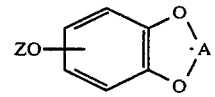

in which
A is —CF$_2$—CF$_2$—, —CF$_2$—CHF— or —CF$_2$—CFCl—,
Z is hydrogen or

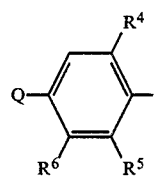

R$^4$ and R$^5$ each independently is hydrogen, halogen, alkyl or halogenoalkyl,
R$^6$ is hydrogen, halogen or alkyl, and
Q is —NO$_2$, —NH$_2$, —NCO or —NCS.

14. A compound according to claim 13, in which Z is hydrogen.

15. A compound according to claim 13, in which Z is

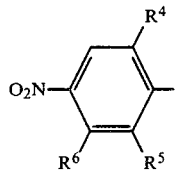
16. A compound according to claim 13, in which Z is
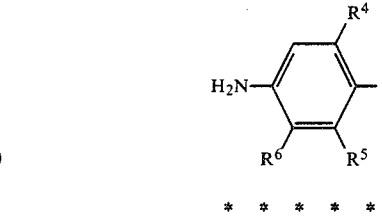
* * * * *